(12) United States Patent
Bhaskar et al.

(10) Patent No.: US 6,495,051 B1
(45) Date of Patent: Dec. 17, 2002

(54) METHODS FOR PREPARING BLOOD OR PLASMA COMPONENT SOLUTIONS WITH IMPROVED CONCENTRATIONS

(75) Inventors: Gautom Bhaskar, Flintshire (GB); Glenn Jorgensen, Allerod (DK)

(73) Assignee: Bristol-Myers Squibb Company, New York, NY (US)

( * ) Notice: Subject to any disclaimer, the term of this patent is extended or adjusted under 35 U.S.C. 154(b) by 223 days.

(21) Appl. No.: 09/677,094

(22) Filed: Sep. 29, 2000

(Under 37 CFR 1.47)

(51) Int. Cl.$^7$ ................................................ A01N 1/02
(52) U.S. Cl. ...................... 210/752; 210/632; 210/782; 210/788; 435/2
(58) Field of Search ................................ 210/632, 749, 210/752, 782, 787, 788; 435/2

(56) References Cited

U.S. PATENT DOCUMENTS 5,738,784 A * 4/1998 Holm et al.
5,824,230 A * 10/1998 Holm et al.
5,849,178 A * 12/1998 Holm et al.
6,099,740 A * 8/2000 Holm et al.

* cited by examiner

Primary Examiner—Betsey Morrison Hoey
(74) Attorney, Agent, or Firm—Theodore R. Furman, Jr.

(57) ABSTRACT

A method for separating a blood component, e.g., fibrin monomer, from blood or plasma. The method utilizes a container with a reaction chamber for receiving the plasma. The reaction chamber is defined by a wall and an agent is supplied to the reaction chamber for converting the fibrinogen content of the plasma into a non-cross-linked fibrin polymer. The method also utilizes a device for centrifuging the reaction chamber with the plasma and the agent to a degree sufficient for separating the non-cross-linked fibrin polymer from the plasma, for depositing the polymer on the outer wall of the reaction chamber, and for expelling the remaining plasma from the reaction chamber. A solvent is supplied to the reaction chamber for dissolving the non-cross-linked fibrin polymer. The solvent is supplied to the reaction chamber in a first amount for dissolving the non-cross-linked fibrin polymer which is less than the total amount of solvent for dissolving the polymer. The remaining solvent is supplied to the reaction chamber in one or more portions to flush the reaction chamber and other portions of the device and recover additional non-cross-linked fibrin polymer.

13 Claims, 4 Drawing Sheets

METHODS FOR PREPARING BLOOD OR PLASMA COMPONENT SOLUTIONS WITH IMPROVED CONCENTRATIONS

BACKGROUND OF THE INVENTION

1. Field of the Invention

The invention relates to methods for separating components from blood or plasma and, more specifically, the invention relates to methods with improved recovery of the blood or plasma component.

2. Description of the Related Prior Art

WO 96/16714 discloses a container for separating a blood or plasma components, e.g., fibrin monomer, from blood or plasma by a centrifugation about a vertical axis. This container comprises a first annular chamber defined by an outer cylindrical wall and an inner cylindrical wall, both walls extending coaxially about a common axis, as well as by a top wall and a bottom wall, where the bottom wall is formed by a piston displaceable within the first chamber. The container further comprises a second chamber accommodated below the first chamber and communicating with the first chamber through a first conduit. The second chamber is defined by the outer cylindrical wall, the bottom wall of the first chamber, and by a second bottom wall. This second chamber serves as reaction chamber for receiving plasma and treating the plasma to obtain the desired component. For example, treatment of plasma fibrinogen with thrombin or a thrombin-like enzyme converts the fibrinogen to fibrin monomer which spontaneously polymerizes to a non-crosslinked fibrin polymer.

Placing this container in a centrifuge for the above-described reaction provides that the non-crosslinked fibrin polymer is separated from the plasma and deposited on an outer wall of the reaction chamber during centrifugation. When the piston is subsequently actuated, the remaining plasma is removed from the reaction chamber. Thereafter, a solvent is added for dissolving the so-deposited non-crosslinked fibrin polymer and forming the desired fibrin monomer solution.

As described in detail in EP 592242, this fibrin monomer solution is extremely useful, for example, in fibrin sealant methods. It is desirable to use devices like those described in U.S. Pat. No. 5,603,845, WO 96/16713, U.S. Pat. No. 5,935,432, WO 96/16714, U.S. Pat. No. 5,824,230, WO 96/16715 and U.S. Pat. No. 5,733,446, the disclosures of which are all incorporated herein by reference, to prepare blood products such as fibrin sealant components immediately at the time of surgery so that autologous blood can be utilized. It may also be desirable from a surgeon's perspective to use sealant products which are relatively uniform from one procedure to another. This is nearly impossible for freshly prepared products, however, since fibrinogen concentration in human blood can vary by ±300% in human patient populations and freshly prepared sealant components from individual sources will also vary. Most humans have fibrinogen levels between 2 and 6 mg/ml of plasma and some humans may have as little as 1 mg/ml and some as much as 10 mg/ml (fibrinogen plasma).

As described in WO 98/30887 and U.S. Pat. No. 5,955,026, the disclosures of which are incorporated herein by reference, a method and apparatus are known which involve introducing blood or plasma into a container having a light transmissive wall and providing a reaction which results in a polymerized form of the component being deposited into the wall. An optical reading of the difference in light transmission through the wall alone and the wall with polymer thereon can be related to the total amount of the component from the blood or plasma sample.

Used in this manner the apparatus and methods disclosed in WO/30887 and U.S. Pat. No. 5,955,026 are useful to determine the concentration of the component in the blood or plasma. Further, by knowing the amount of solvent or buffer to be used to solubilize the polymerized component to yield the desired component solution, the concentration of the resulting solution is readily available. Still further, when the optical determination of the concentration of the component in blood or plasma (or the determination of the amount of polymerized component) is made, this data can be used to control the amount of buffer or solvent used to solubilize the polymer to prepare solutions of desired concentrations. Still further, when the buffer or solvent is also used so that the resulting solutions are of a specific value or range of values of pH, limits on the minimum and maximum amount of buffer or solvent used can be employed. For example, when a plasma fraction is reacted to form a fibrin polymer and a pH-4 acetate buffer is used to solubilize the polymer to form a desired fibrin monomer solution, minimum and maximum amounts of buffer can be programmed into the process and apparatus to keep the resulting pH within a desired range, e.g., 4.0–4.5. The methods described in WO 98/30887 can provide fibrin monomer solutions of about 20 mg/ml ±25% while simultaneously maintaining pH value between 4.0–4.5. This represents a remarkable 10-fold increase in reproducibility of freshly prepared or autologous fibrin monomer solution. It is also important to note that the optical sensing apparatus and methods described in WO 98/30887 determine amounts/concentrations of components in a container rotating at high speeds, e.g., up to 9000–10,000 RPM rather than taking an optical measurement in a fixed position.

Apparatuses and methods such as those discussed above, while advantageous, may still not recover all of the fibrin polymer deposited on the container walls. Accordingly, it would be advantageous to ensure removal of all or substantially all of the polymerized form of the component deposited on the wall of the container in order to maximize the amount of recovery of the component.

SUMMARY OF THE INVENTION

Accordingly, an object of the invention is to provide a method whereby supply of solvent is controlled and, in particular, solvent is applied in multiple steps to maximize recovery of the polymerized form of the desired component.

In order to achieve the foregoing object and other objects, there is provided a method for preparing a solution of a blood or plasma component with improved recovery of the blood or plasma component. The method in accordance with the present invention includes the step of subjecting blood or plasma to conditions for catalyzing formation of a polymerized form of said component of said blood or plasma. The polymerized form of the component is then recovered, and an initial amount of a solvent solution is added to the recovered polymerized form of the component to dissolve it. The initial amount of solvent is an amount less than a predetermined total amount of buffer solution for dissolving all of the recovered polymerized form of the component. Additional solvent is added to the recovered polymerized form of the component. The additional solvent is added to the recovered polymerized form of the component in an amount equivalent to a difference between the predetermined total amount of solvent and the initial amount of solvent added to dissolve the polymerized form of the component.

BRIEF DESCRIPTION OF THE DRAWINGS

The invention is described in greater detail below with reference to the accompanying drawings, in which.

DETAILED DESCRIPTION OF THE PREFERRED EMBODIMENTS

The present invention provides methods for preparing solutions of a blood or plasma component of known or controlled concentrations and with improved recovery of the component. This provides the unique ability to prepare such solutions in an automated centrifuge unit in under 30 minutes so that freshly prepared, and preferably autologous, components can be utilized. The possible disadvantage of using freshly prepared solutions or components, i.e., the fact that component levels may vary from patient to patient, is overcome in the present invention. The concentration of a component solution, e.g., a fibrin monomer solution, is improved.

Throughout this application the present invention is described with regard to preferred embodiments, e.g., preferred apparatus, containers and processes useful for preparing fibrin monomer solutions from whole blood or plasma. However, it should be readily understood by those skilled in the art that other blood or plasma components could also be prepared or extracted using the general methods described herein.

Figure 1:
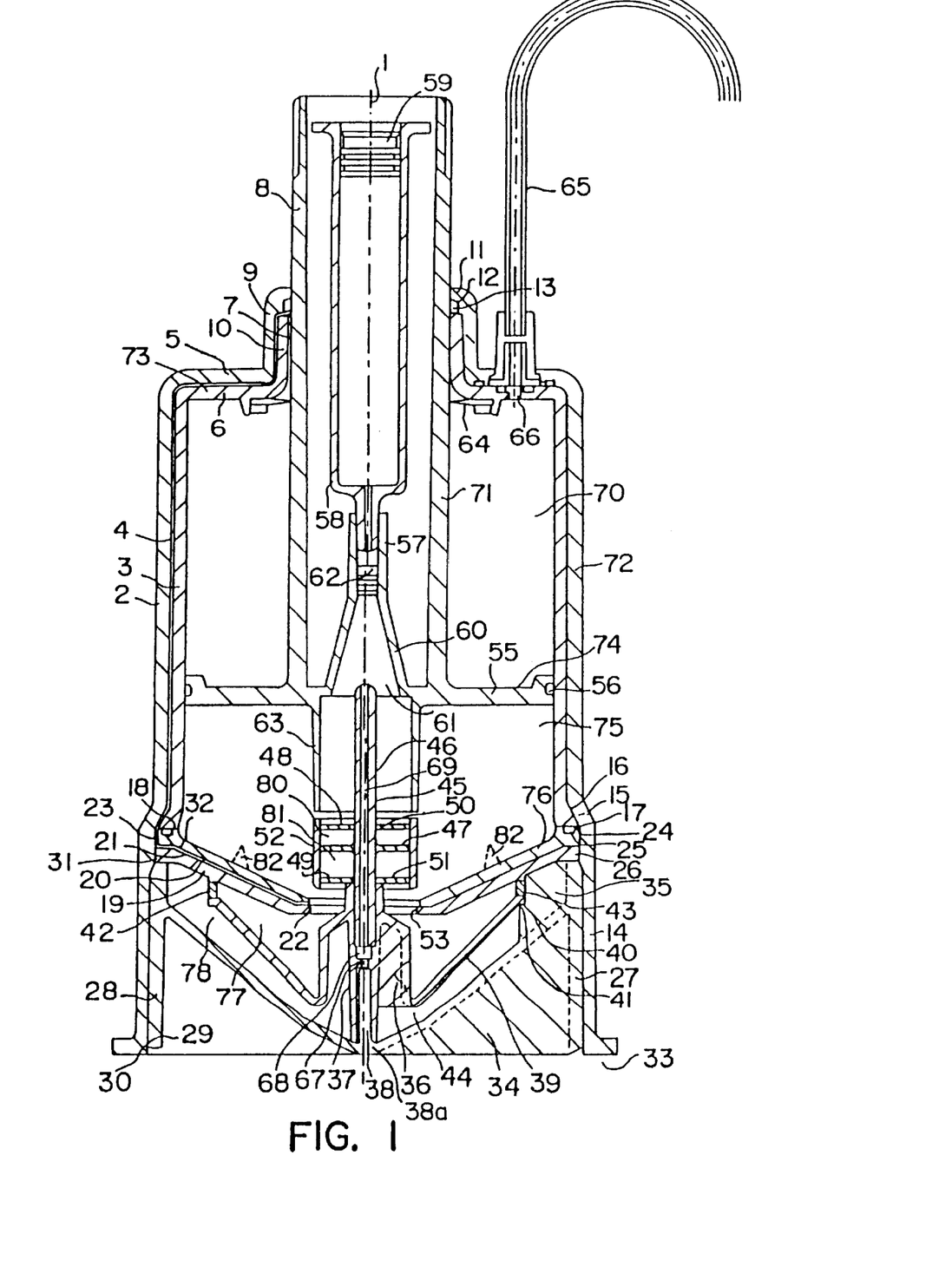
FIG. 1 is an axial sectional view of a container for separating fibrin monomer from blood plasma.

Referring now to the drawings wherein like numbers indicate like elements, there is shown in FIG. 1 a container. The container is built of parts allowing for rotation symmetry and allowing for the container to be placed in a centrifuge apparatus shown in FIG. 2 so as to be centrifuged about a central axis 1. In this regard, known liquid separation apparatus and methods suitable for use in the present invention are disclosed in U.S. Pat. Nos. 5,603,845, 5,738,784 and 5,750,657, the disclosures of which are each herein incorporated by reference.

The container of the present invention is preferably of a medical grade plastic material, and polycarbonate material is preferred. For reasons that are discussed below, the material may be light transmissive in a certain wave length range. The container comprises an outer container part 2 and an inner container part 3 which completely fit into each other and everywhere closely abut one another apart from the portion where an axially extending intermediary channel 4 is provided. The channel 4 is provided by a groove shaped in inner container part 3. Container parts 2 and 3 include bottoms 5 and 6, respectively, the bottoms defining a central opening 7 allowing passage of a piston rod 8. About opening 7, the two container parts include axially extending portions 9 and 10, respectively, which extend closely to hollow piston rod 8 in a direction away from the interior of the container parts. Outer container part 2 abuts hollow piston rod 8 along a short radially extending flange 11 provided with a recess 12 receiving a sealing ring 13.

As illustrated in FIG. 1, channel 4 continues between the inner and the outer container parts all the way from the outer cylindrical walls of the inner and the outer container parts along bottoms 5 and 6 and axial portions 9 and 10 to the opening immediately below sealing ring 13 in opening 7. Axial portion 10 of inner container part 3 abutting the opening 7 is dimensioned such that a narrow, but free passage exists to the interior of the container parts 2 and 3 about hollow piston rod 8.

Outer container part 2 comprises a cylindrical portion of a uniform diameter. Downwardly, when seen relative to FIG. 1, this portion continues into a cylindrical portion 14 of a slightly larger diameter through a short transition portion 15 forming a frusto-conical inner surface 16. Inner container part 3 ends at the location where transition portion 15 of outer container part 2 continues into cylindrical portion 14 of a larger diameter. The lower end of inner container part 3 comprises an outer surface 17 of a frusto-conical form matching the form of the frusto-conical surface 16 on the inner side of outer container part 2. An outer and an inner annular disk 19 and 20, respectively, are provided immediately below the lower end of inner container part 3, which ends in a radial surface 18. These disks closely abut one another apart from the fact that they define therebetween a channel 21 extending in an axial plane from a central opening 22 and forwards to the inner side of outer container part 2, where the channel 21 communicates with the channel 4 between the outer container part 2 and the inner container part 3 through an axially extending portion 23. Channel 21 and axially extending portion 23 are suitably provided by means of a groove in the side of inner disk 20 facing outer disk 19. The two disks 19 and 20 are shaped with such an oblique course that they comprise substantially inner and outer frusto-conical surfaces and thereby incline downwards towards central opening 22 in a direction away from opening 7 of hollow piston rod 8 in outer container part 2 and inner container part 3. Inner disk 20 also includes a radial surface 24 abutting the adjacent radial surface 18 on inner container part 3. Radial surface 24 of the inner disk 20 is provided with a recess 25 for receiving a sealing ring 26.

The two disks 19 and 20 are maintained in position in abutment against the radial surface 18 of the inner container part 3 by means of a cover 27 closing outer container part 2 in the downward direction. Cover 27 comprises a circumferential sleeve-shaped portion 28 adapted to closely abut the inner side of the outer container part 2, to which it is secured in a suitable manner, such as by way of a snap-action engagement between a circumferential rib 29 on the outer side of sleeve 28 and a corresponding circumferential groove 30 on the inner side of the outer container part 2. A sealing connection is ensured by means of a sealing ring 31 in a circumferential recess 32 at the outer periphery of outer disk 19. Cover 27 also includes a relatively thin wall 32 adapted to form the lower bottom of the container in the position shown in FIG. 1. Wall 32 extends substantially along a course parallel to outer and inner disk 19 and 20 in such a manner that wall 32 extends from the inner side of the sleeve 27 in a portion adjacent the disks 19 and 20 and downwards towards a portion substantially on a level with the lower rim 33 of the outer container part 2. In order to reinforce this relatively thin wall 32, a reinforcing radial rib 34 is provided at regular intervals, only one of the ribs appearing from FIG. 1a. Rib 34 is shaped partly with a portion placed outside wall 32 and partly with a portion placed inside wall 32. The latter inside portion is designated reference numeral 35 and is shaped such that it abuts the bottom side of outer disk 19 with the result that it assists in maintaining the disks 19 and 20 in a reliable position.

Partition 36 is located between outer disk 19 and cover 27. Partition 36 comprises a central pipe length 37 which is mounted on a pin 38 projecting axially inwards and being shaped integral with wall 32 of cover 27. Pipe length 37 is shaped integral with a circumferential wall disk 39 extending outwardly from pipe length 37 in such a manner that initially it inclines slightly downwards towards wall 32 of cover 27 whereafter it extends along a short axial course so as to continue into a course extending substantially parallel to wall 32 of the cover. Wall disk 39 ends in a short radially extending periphery 40 resting on a shoulder 41 on rib portions 35 on cover 27. An annular filter unit 42 is located between outer periphery 40 of wall disk 39 and the bottom side of outer disk 19. Annular filter unit 42 abuts a substantially radially shaped surface 43 on the adjacent outer side of the outer disk 19.

In order to ensure stability in partition 36, reinforcing radial ribs designated reference numeral 44 are located between pipe length 37 and wall disk 39.

A capsule designated the general reference numeral 45 is secured in the end opposite cover 27 of pipe length 37 of partition 36. This capsule comprises an elongated pipe length 46 shaped integral with a radial disk 47 and carrying two additional radial and annular disks 48 and 49. Radial disks 48 and 49 are secured by way of friction fit on their respective side of the fixed disk 47. Loose disks 48 and 49 are positioned at their respective distance from fixed ring 47 by means of circumferential shoulders 50 and 51 respectively, on the pipe length 46. The three disks 47, 48, and 49 are all of the same outer diameter and carry along their respective peripheries a circumferential, displaceably mounted sleeve 52.

As illustrated in FIG. 1, lower disk 49 abuts the upper end of the pipe length 37 of partition 36, whereby the position of the capsule 45 in the axial direction is determined. This position is furthermore determined in such a manner that when displaced in the axial direction the displaceable sleeve 52 of the capsule enters a sealing engagement by its lower end, with innermost edge 53 on outer disk 19 in central opening 22. In this position of sleeve 52, a communication still exists between the space inside inner disk 20 surrounding sleeve 52 and the inlet opening to channel 21 between outer disk 19 and inner disk 20. The axial length of displaceable sleeve 52 is adapted such that engagement with outer disk 19 occurs before the upper end of sleeve 52 disengages fixed ring 47 during the axial downward displacement of sleeve 52. The inner diameter of the sleeve 52 is also adapted to the outer diameter of the axially extending portion of wall disk 39 of partition 36 in such a manner that a continued downward displacement of the sleeve 52 towards the cover 27 causes sleeve 52 to fixedly engage partition 36 once it has disengaged the outer disk 19. The length of the axial portion of partition 36 corresponds also to the axial length of sleeve 52 in such a manner that sleeve 52 in the lowermost position is substantially completely received by partition 36.

As illustrated in FIG. 1, the hollow piston rod 8 comprises a circumferential piston 55 inside outer container part 2 and inner container part 3, piston 55 sealingly engaging the inner side of the inner container part 3 through a sealing ring 56.

Luer-coupling 57 is located inside hollow piston rod 8 for receiving a conventional syringe 58 with a piston-acting plug 59 for acting on the content of syringe 58. Coupling 57 is shaped substantially as a pipe length communicating with a central opening 61 in piston 55 through a frusto-conical portion 60. Pipe length 57 is provided with a radially inwardly projecting web 62 for directing fluid leaving syringe 58 away from an axial path and thereby round the elongated pipe length 46 therebelow inside capsule 45. The latter pipe length 46 is of such a length and such dimensions that it can sealingly engage, the pipe length 57 inside the hollow piston rod 8 when the piston 55 is in its lowermost position near cover 27. In order to promote the above sealing connecting, the inner side of the pipe length 57 is formed with a gradually decreasing diameter at the end adjacent the piston 55.

Axially projecting skirt 63 is formed integral with piston 55 about central opening 61 of the piston. Skirt 63 is shaped with such a diameter and such a length that by a suitable displacement of piston 55 it can activate the above displacement of displaceable sleeve 52 of the capsule 45 into the positions in which it engages inner rim 53 of central opening 22 through two disks 19 and 20, followed by an engagement of partition 36.

Resilient, annular lip seal 64 is secured about hollow piston rod 8 at the top inside container parts 2 and 3. This lip seal 64 is adapted to prevent an undesired passage of fluid from the interior of the container parts 2 and 3 to channel 4, but it allows passage of fluid when a force is applied through piston 55.

As indicated at the top of FIG. 1, a connection is provided to a hose 65 through an opening 66 in outer and inner container parts 2 and 3, respectively. This connection is known and therefore not shown in greater detail, but it allows an interruption of the connection to the hose when desired. In addition, an air-escape opening with a suitable filter is provided in a conventional manner and therefore neither shown nor described in greater detail.

Passage 69 is provided from the area between partition 36 and cover 27 and all the way upwards through the interior of pipe length 37 of partition 36 and through the interior of pipe length 46 of capsule 45. Passage 69 allows a transfer of fluid to syringe 58 from this area when pipe length 46 is coupled to pipe length 57 in the interior of piston rod Passage 38a is provided at the lowermost portion of pin 38 in cover 27 by pin 38 being shaped with a plane, axial surface, the pin being of a substantially circular cross section. As a result, a space is provided between the pin and the adjacent portion of the inner side of the pipe length 37. Area 67 is provided immediately above pin 38 where partition 36 presents a slightly reduced inner diameter. In this manner, it is possible to place a small filter 68 immediately above this area, whereby the fluid must pass the filter before it enters pipe length 46 of capsule 45.

The described container comprises a first annular chamber 70 defined inwardly by hollow piston rod 8 forming a cylindrical inner wall 71, and outwardly by a cylindrical outer wall 72 formed by outer container part 2 and inner container part 3. When in the conventional use position of FIG. 1, annular chamber 70 is upwardly defined by top wall 73 formed by bottoms 5 and 6, respectively, of outer container part 2 and inner container part 3. Downwardly, annular chamber 70 is defined by a bottom wall 74 formed by piston 55. Second chamber 75 is defined below piston 55, the second chamber outwardly being defined by the same cylindrical outer wall 72 as first chamber 70. Downwardly, second chamber 75 is defined by a second bottom wall 76 formed by outer disk 19 and inner disk 20. Capsule 45 is centrally accommodated in the interior of second chamber 75. Third chamber 77 is provided below second bottom wall 76, and third chamber 77 is defined by partition 36 and annular filter unit 42. In addition, third chamber 77 communicates with second chamber 75 through the passage formed by central opening 22 in outer disk 19 and inner disk 20. Finally, fourth chamber 78 is provided below partition 36, fourth chamber 78 being defined downwardly by wall 32 of cover 27 and furthermore by portions of sleeve 28 of cover 27 and the bottom side of outer disk 19.

As described above, the container in question is primarily suited for separation of a component, such as fibrin monomer from blood and, for this purpose, second chamber 75, and preferably upper chamber 80 of capsule 46, is in advance filled with a suitable enzyme, which can catalyze the cleavage of fibrinopeptides A and/or B from fibrinogen, i.e., convert fibrinogen to fibrin, such as batroxobin. As is understood from EP No. 592,242 and U.S. Pat. No. 5,750,657, the disclosures of which are incorporated herein by reference, any thrombin-like enzyme can be employed. Such enzymes include thrombin itself or any other material with a similar activity, such as Ancrod, Acutin, Venyyme, Asperase, Botropase, Crotabase, Flavorxobin, Gabonase, and the preferred Batroxobin. Batroxobin can be chemically bound to biotin, which is a synthetic substance allowing the batroxobin to be captured in a conventionally known manner by means of avidin in an avidin-agarose composition. Accordingly, avidin-agarose is located in lowermost chamber 81 of the capsule. Both the biotin-batroxobin composition and the avidin-agarose composition are relatively easy to fill into respective chambers 80 and 81 inside capsule 45 before the capsule is placed inside the device.

Finally, syringe 58 is located in piston rod 8, syringe 58 containing a pH-4 buffer prepared from an acetate diluted with acetic acid. Syringe 58 is later used for receiving the desired fibrin monomer solution.

Another buffer known from the prior art can also be used. The redissolving buffer agent can be any acid buffer solution preferably those having a pH between 1 and 5. Suitable examples include acetic acid, succinic acid, glucuronic acid, cysteic acid, crotonic acid, itaconic acid, glutonic acid, formic acid, aspartic acid, adipic acid, and salts of any of these. Succinic acid, aspartic acid, adipic acid, and salts of acetic acid, e.g., sodium acetate are preferred. Also, the solubilization may also be carried out at a neutral pH by means of a chaotropic agent. Suitable agents include urea, sodium bromide, guanidine hydrochloride, KCNS, potassium iodide and potassium-bromide. Concentrations and volumes of such acid buffer or such chaotropic agent are as described in EP No. 592,242.

During or immediately after the supply of blood, piston rod 8 is pushed so far into the interior of the container that displaceable sleeve 52 of the capsule 45 is moved downwards into a sealing engagement in the through passage through bottom wall 76 and to second chamber 77. As a result, access is simultaneously opened to the biotin-batroxobin composition inside the uppermost chamber 80 of the capsule.

When the container is ready for use, a blood sample is fed into the first chamber through a needle not shown and hose 65 in a conventional manner, the blood sample preferably being admixed with an anticoagulant also in a conventional manner. During the feeding of the blood through hose 65 and opening 66 into the interior of first chamber 70, air is removed from the chamber in a conventional manner. After the feeding of blood, hose 65 is removed, and opening 66 is sealingly closed. Subsequently, the container with the blood is placed in a centrifuge apparatus which inter alia assists in sealingly compressing the various portions. The centrifuge apparatus is described further below and causes the container to rotate about axis of rotation 1. As a result of the centrifuging, the blood is separated in first chamber 70 into a plasma fraction settling radially inside the remaining portions of the blood, the remaining portions containing the red and the white blood cells disposed in an outermost portion of chamber 70. As described in EP No. 592,242, the platelets can be present in either the plasma fraction or the fraction disposed in the outermost portion of chamber 70, as desired, by varying the speed and time of centrifugation.

When the interfaces between the plasma and the remaining portions of the blood have been stabilized, i.e., when the separation is complete, a reduction of the volume of first chamber 70 is initiated by piston rod 8 and consequently piston 55 being pulled out. As a result, first a possible inner layer of air passes through channels 4 and 21 into second chamber 75, and a further moving of piston 55 results in the plasma passing to second chamber 75. Movement of piston 55 is stopped when the entire layer of plasma has been forced into second chamber 75, i.e., when the interface between the plasma fraction and the remaining portion of the blood disposed in the outermost portion of chamber 70 reaches the inner wall 71 of first chamber 70.

Figure 2:
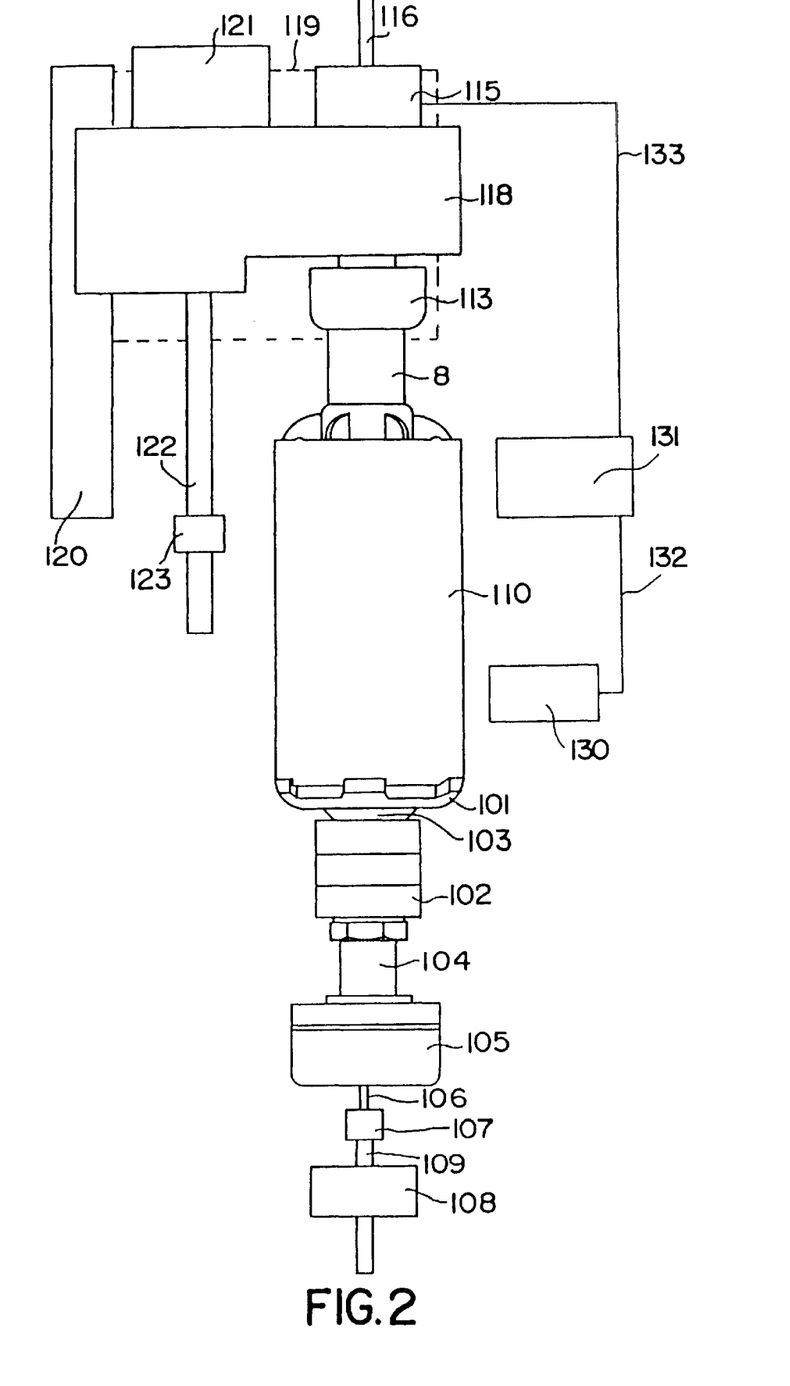
FIG. 2 is a diagrammatic view of an apparatus during the handling of a container of the type shown in FIG. 1.
Figure 2A:
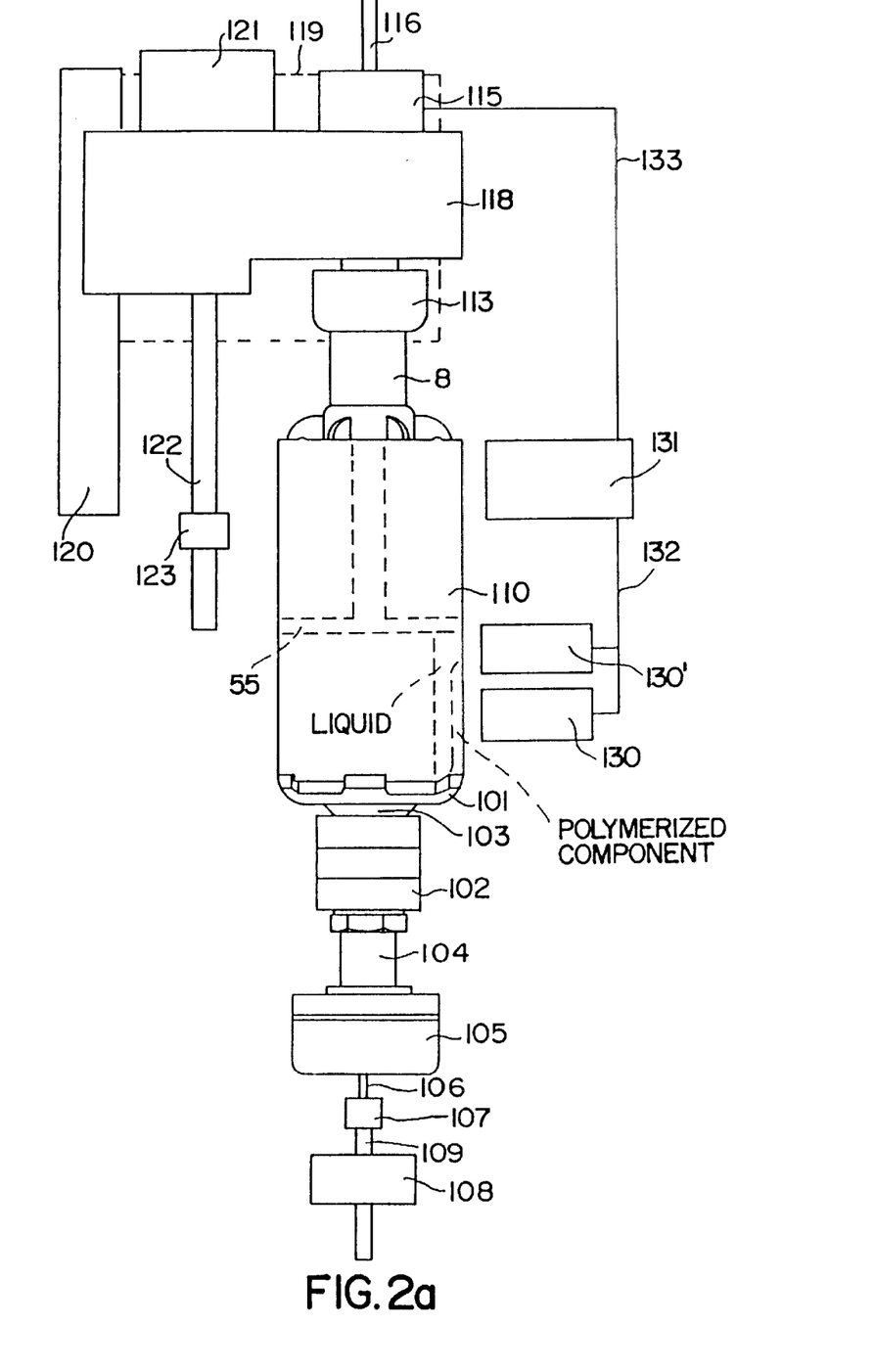
FIG. 2a is a second diagrammatic view of an additional apparatus during the handling of a container of the type shown in FIG. 1.

As described in WO 98/30887 and U.S. Pat. No. 5,955,026, the feeding of the amount of pH-4 buffer and consequently the activation of syringe 58, can be according to a predetermined, fixed amount of buffer to be added or can be carried out in response to the amount of non-cross-linked fibrin polymer present in second chamber 75 of container 110. That is, the amount of fibrin polymer present in second chamber 75 can be measured by a photometer 130 stationarily arranged in the apparatus in front of second chamber 75. The photometer may comprise a light emitting device and a light sensor (not shown) arranged so that light transmission intensity through the wall of container 110 can be measured. Any light emitter can be used depending upon the material of the wall. Preferred light emitters are in the wave length range of 400–1100 nanometers. Preferred are LED's having wave length of 920 or 654 mm. Model SFH460 from Siemens is suitable for this purpose. As described in WO 98/30887, photometer 130 measures the amount of fibrin polymer on the outer wall of second chamber 75 by observing the decrease in light intensity transmitted through the chamber wall having polymer thereon as compared to a reference reading of the light transmittal through the wall alone. The transmission readings can be carried out continuously at least during the period beginning immediately prior to the addition of pH-4 buffer and ending after the addition has been terminated. In the beginning of this period, the thickness and consequently the amount of fibrin polymer is registered, and based thereon the amount of pH-4 buffer to be added is determined. The latter determination of amount of pH-4 buffer is performed in control unit 131 receiving information on the measured values of the photometer through conduit 132. Subsequently, control unit 131 activates motor 115 through conduit 133 so as to drive spindle 116 and consequently the activating bar which in turn activates piston 59 of syringe 58.

Figure 3:
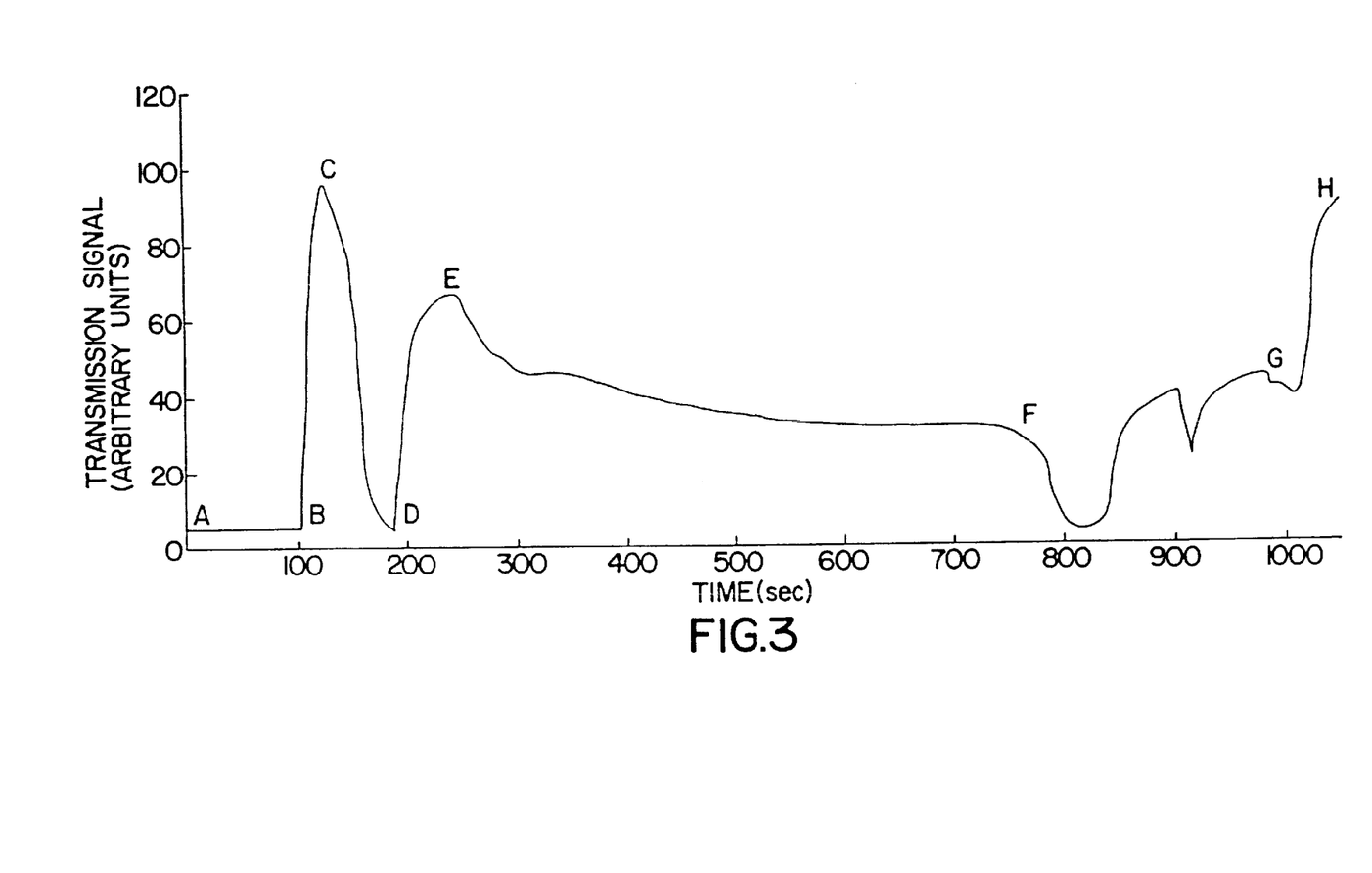
FIG. 3 is a graph showing measurements of a photometer versus time.

As also described in WO 98/30887 and U.S. Pat. No. 5,955,026 and illustrated in FIG. 3, a second photometer 130' can be utilized. As described above, the light transmission of the light emitter is preferably continuous during the process of depositing the component polymerized from the liquid plasma/serum onto the light transmissive chamber wall. FIG. 3 shows, in partial crossection, the relationship of the polymerized component, the liquid (plasma or serum) and piston 55 during centrifugal deposition of the polymerized component onto the wall. Since the liquid can interfere with the accuracy of the data observed by the first photometer or 130, second photometer 130' may be placed in a position where it is expected to transmit light through the wall and liquid, but not through the polymerized component. A comparison of these readings can eliminate the possible interference of the liquid in the accuracy of the readings.

It is also useful to note that the one or more photometers, 130 and 130', may be modulated so that the detector portion remains "on" but the LED's pulse "on and off". In this way, the detector portion of the photometers can take into account (and be programmed to disregard) background light which may be in the vicinity of the present apparatus. The modulation of the LED's is preferably at a frequency which is not equal to, or is not a multiple of, the rotational speed of the centrifuge.

FIG. 3 illustrates a graphing of the measurings of the photometer versus the time. The graphing shows the measurings of the photometer from the starting of the centrifuge apparatus to the end of the supply of pH-4 buffer to second chamber 75. The portion of the graphing from A to B shows the measurements taken when piston 55 is in a lower position and blocks the passage for the signal of the photometer. At C the piston has been raised, and the photometer is measuring light transmission through the plastic material alone of which the container is made while second chamber 75 is still empty. The measurement at C is used for calibrating the photometer so that the succeeding measurements take the translucency of container 110 into account, the translucency varying from container to container. From C to D the plasma is transferred to second chamber 75 together with some air. From D to E the air in the plasma is removed, and the enzyme, such as batroxobin, is released in second chamber 75. Around the point E, the measurements also provide information on features, such as the concentration and clarity of the blood, which may vary from blood portion to blood portion. From E to F, the non-crosslinked fibrin polymer is released from the plasma fraction. From F to G, the remaining relatively fluid portion of the plasma fraction is transferred to first chamber 70 by air first being drawn from first chamber 70 to the second chamber 75 by the piston 55 being raised. Then the remaining fluid plasma fraction is transferred to the first chamber 70 by piston 55 being lowered. During the latter period, more centrifugations and activations of the piston are performed with the result that all the fluid plasma fraction is removed from the fibrin polymer. At G the measurement shows the thickness of the pure fibrin polymer and thereby the amount of fibrin polymer present in second chamber 75. Based on the latter measurement, the amount of pH-4 buffer to be added is determined. From G to H, the dissolving of the fibrin polymer by means of the supplied pH-4 buffer takes place.

When the desired amount of pH-4 buffer has been added, the activation of the piston 59 of the syringe 58 is stopped. The amount of pH-4 buffer optionally remaining in the syringe 58 is not expelled until later on in the second chamber, wherein it is expelled immediately before pipe length 46 is coupled to syringe 58 for the suction up of fibrin monomer solution from the fourth chamber 78. As described in WO 98/30887, the amount of fibrin polymer deposited on the wall can be determined using a photometer comprising a light source, e.g., LED, laser or other light emitter, and sensor arranged to measure the decrease in light transmission through the chamber wall as the fibrin is deposited thereupon. Any convenient photometer can be employed and the wave length range of the light source is selected to be sensitive in the range of the material being deposited and taking the material of the wall into consideration. In the case of depositing fibrin polymer into the chamber wall, a 654 nanometer wave length light emitting diode (LED) has been found useful. The decrease in light transmission is arrived at by taking a reference reading (R) of the light transmission through the chamber wall prior to fibrin polymer deposition and thereafter measuring the final light transmission (F) after fibrin polymer deposition is complete. A correlation between the natural log of a comparison of these light transmission intensities and the fibrin mass can be expressed as $$\text{Fibrin mass} = C \cdot \ln(R/F) \quad (1)$$

where C=a component coefficient, e.g., a fibrin coefficient.

The fibrin coefficient (C) can be established experimentally by stopping the process and measuring the fibrin mass in a series of runs for observed values of ln R/F. By plotting where the experimentally measured fibrin mass versus observed light transmission decreases it is possible to define a fibrin coefficient (the slope of the plotted line).

Thereafter, measured decreases in light transmission expressed as ln (R/F), multiplied by the fibrin coefficient, are indicative of the amount of fibrin polymer formed and knowledge of a predetermined amount of solvent or buffer to be used to solubilize the fibrin polymer provides the concentration of the resulting fibrin monomer solution. Obviously, the component coefficient would have to be re-established for different processes and different blood or plasma components. This concentration can be expressed as $$\text{Conc} = \frac{\text{Fibrin mass}}{VT} \quad (2)$$

where Conc is concentration, VT is total volume and where VT=Fmass+VB where VB is the value of buffer or solvent added to solubilize the fibrin.

In accordance with the process described above, it has also been found that some of the serum and other proteins from the blood or plasma source may become trapped in and around the fibrin polymer deposited on the wall. Indeed, the actual fibrin mass may only be a small portion of the mass of fibrin serum deposited. This is dependent upon the process used, i.e., can vary according to the speed (RPM) and time of centrifugal spinning during the deposition of the fibrin polymer onto the wall. For example, in centrifuging the plasma (obtained from 120 ml of blood) at about 9000 RPM for about 5–10 minutes in the presence of sufficient quantities of enzyme which converts fibrinogen to fibrin, it has been found that the actual fibrin mass is only about 5–10% of the mass of fibrin/serum which is deposited on the wall. In the case where serum is present, concentration can be expressed as $$\text{Conc} = \frac{\text{Fibrin mass}}{VS + VB} \quad (3)$$

where VS=the volume of fibrin and serum retained in the fibrin.

It has been determined experimentally that the volume of fibrin+serum (VS) has a linear relationship with the fibrin mass which can be expressed as $$VS = a + b \cdot \text{Fibrin Mass} \quad (4)$$

where
a=volume of serum only
b=volume of fibrin per mg of fibrin+serum

Both (a) and (b) can be determined experimentally by plotting measured fibrin+serum mass versus fibrin mass (a) being the y-intercept and (b) being the slope of the plotted line.

This provides the relationship $$Conc = \frac{Fibrin\ mass}{VB + a + b} \cdot Fibrin\ mass \qquad (5)$$

By substituting formula (1) for "Fibrin mass" at both instances in formula (5) the following expression is provided $$Conc = \frac{C \cdot \ln(R/F)}{VB + a + b} \cdot C\ \ln(R/F) \qquad (6)$$

Thus, for a given process where C, a and b have been experimentally determined as described above, and where the volume of solubilizing buffer (VB) is known, the concentration of a blood component solution, e.g., a fibrin monomer solution, can be determined by observing the decrease in light transmission through a deposited polymer from which the solution is made and utilizing formula (6) above.

In other words, a microprocessor driven apparatus can be programmed with the formula and experimentally-determined constants above for a given process such that signals from photometer readings through the chamber wall before and after said polymerized component is deposited thereupon will enable the microprocessor to determine the concentration of the blood component solution which will result from solubilization of the polymerized component with a known quantity of buffer or solvent. Further, metered dispensing can be provided for the buffer or solvent so that varying amounts of buffer or solvent can be used to solubilize the polymerized blood component into the desired solution. In this way, a solution of a desired concentration of the blood component can be produced regardless of the initial concentration of the component in the blood by determining the amount of fibrin polymer (and serum) deposited and introducing an amount of buffer in response to this information which will result in the same concentration from run to run. This is accomplished by re-expressing formula (6) to solve for the amount of buffer (VB) needed to produce a solution of desired concentration (Conc) as below $$VB = C \cdot \ln\ (R/F)((1/Conc)-b)-a \qquad (7)$$

Thus, in accordance with the foregoing, there is provided apparatus and methods for producing solutions of blood components, e.g., fibrin monomer solutions, at constant desired concentrations even when starting with blood or plasma having variable initial concentrations of fibrinogen, e.g., 1–10 mg/ml, as may be found in the human population.

In accordance with the present invention, an initial amount of solvent or buffer less than the total amount of solvent or buffer (VB) is applied to second chamber 75 to solubilize the non-cross-linked fibrin polymer present therein. As used herein, the terms "solvent" and "buffer" are intended to be interchangeable and are defined as materials that solubilize non-cross-linked fibrin polymer in accordance with the present invention. Further, they are intended to include the chaotropic agents discussed above.

Subsequently, a flushing amount of the buffer is applied to second chamber 75 to capture non-cross-linked fibrin polymer remaining therein and also non-cross-linked fibrin polymer trapped in filter 42. That is, in accordance with the present invention, a so-called "safe" amount of solvent is introduced into second chamber 75, the safe amount of solvent being an amount that will ensure solubilization of the non-cross-linked fibrin polymer without or substantially without precipitation of fibrin polymer therefrom. For example, for an acetate buffer the upper limit of the pH of the fibrin solution will be a pH of 4.60. Above this pH, precipitation of fibrin may occur. Thus, for acetate buffer an amount is utilized that will result in a pH of the fibrin solution of from 3.9 to 4.60, the pH of the fibrin and any blood serum contained therein generally being 7 or neutral. Thereafter, the remaining amount of the total volume of the buffer (VB) is added to solubilize or "flush" the remaining non-cross-linked fibrin polymer in second chamber 75 and to solubilize or capture non-cross-linked fibrin polymer present in filter 42 due to the previously conducted filtration steps.

The amount of the portion of the total solvent or buffer volume (VB) added initially in accordance with the present invention will, as would be recognized by one skilled in the art, depend on the "strength" of the buffer solution. That is, the amount will depend on the ability of the solvent or buffer to maintain the pH of the resulting fibrin solution within a pH range that maintains the fibrin in solution without or substantially without precipitation of the fibrin. For example, this portion may range from 20 to 80 vol. % of the total volume of the solvent or buffer (VB). A solvent or buffer having a relatively strong ability to maintain fibrin in solution will enable the use of a lower amount of the total solvent or buffer volume (VB) initially because when such a solvent or buffer is mixed with the fibrin and any blood serum that may be present therein, a fibrin solution having a suitable pH that avoids fibrin precipitation, will result. On the other hand, a low "strength" solvent or buffer solution will require the use of a relatively higher percentage of the total volume of the solvent or buffer (VB) initially in order to achieve a fibrin solution having a pH which will avoid precipitation fibrin.

Also, in accordance with the present invention, the non-cross-linked fibrin polymer may be solubilized by utilizing an initial portion of the total volume of the solvent or buffer solution (VB), as described above, and then the remaining amount of the total volume may be added in multiple steps. For example, about 60% of the total volume of the solvent or buffer (VB) may be initially added to solubilize the fibrin, and then the remaining amount of the total volume of the solvent or buffer (VB) may be added in two or more separate steps. That is, the remaining 40% of total solvent or buffer volume (VB) may be added in two steps, one step containing 20% of the total solvent or buffer volume (VB) and another step containing the remaining 20% of the total solvent or buffer volume (VB). In this manner, the addition of the remaining amount of the total solvent or buffer volume (VB) after the initial addition may be divided into any suitable number of additions of solvent or buffer solution in order to recover non-cross-linked fibrin polymer from second chamber 75 and filter 42 to any desired degree.

In general, the process in accordance with the present invention may be carried out as follows. As described above, the amount of the total solvent or buffer volume (VB) is calculated based upon the amount of fibrin polymer on the outer wall of second chamber 75 as measured using photometer 130. Syringe 58 is then activated to initially feed a portion, for example, 80 vol. %, of the total solvent or buffer volume (VB) to second chamber 75, the exact amount of this portion being predetermined by appropriate consideration the strength of the buffer. The non-cross-linked fibrin polymer is then washed to prepare a fibrin solution of suitable pH, and this solution is filtered using filter 42 in the manner described above in order to capture enzyme used to catalyze the cleavage of fibrinopeptides A and/or B from the fibrinogen contained in the blood or plasma and form the non-cross-linked fibrin polymer. Syringe 58 is then activated again, this time to feed the remaining portion of the total solvent or buffer volume (VB) in either one or more steps to second chamber 75 to solubilize all or substantially all of the non-cross-linked fibrin polymer remaining on the walls of second chamber 75. This additional fibrin solution containing additional non-cross-linked fibrin polymer recovered from second chamber 75 is then filtered in the manner discussed above using filter 42. This filtration advantageously recovers additional non-cross-linked fibrin polymer trapped in filter 42. The additional fibrin is then combined with the fibrin solution from the initial solubilization of the non-cross-linked fibrin polymer using the initial portion of the total volume of the solvent or buffer (VB). After removal of any unused buffer in syringe 58, the combined fibrin solutions are then taken up into syringe 58 in the manner described above and are suitable for use in a fibrin sealant or for any other desired purpose.

In accordance with the present invention, the amount of fibrin recovered is advantageously increased resulting in fibrin solutions having increased fibrin concentrations. Any increase in fibrin recovery, especially those achievable in accordance with the present invention, is particularly advantageous since as discussed above, fibrinogen concentration in human blood can vary by ±300% in human patient populations and freshly prepared sealant components from individual sources will also vary. In particular, significantly improved fibrin solutions are obtainable for freshly prepared sealant components for humans having low fibrinogen levels.

Although the present invention has been described in connection with a preferred embodiment thereof, many other variations and modifications and other uses will become apparent to those skilled in the art without departing from the scope of the invention. It is preferred, therefore, that the present invention not be limited by the specific disclosure herein, but only by the appended claims.

What is claimed is:

1. A method for preparing a solution of a blood or plasma component, comprising the steps of:

subjecting blood or plasma to conditions for catalyzing formation of a polymerized form of said component;

recovering said polymerized form of said component;

adding an initial amount of solvent to said recovered polymerized form of said component to dissolve said polymerized form of said component, said initial amount of solvent being an amount less than a predetermined total amount of solvent for dissolving all of said recovered polymerized form of said component; and adding additional solvent to said recovered polymerized form of said component, said additional solvent being added to said recovered polymerized form of said component in an amount equivalent to a difference between said predetermined total amount of solvent and said initial amount of solvent added to dissolve said polymerized form of said component.

2. The method according to claim 1, further comprising the step of spinning said recovered polymerized form of said component in a chamber of a centrifuge apparatus while said solvent is added to said chamber to dissolve said polymerized form of said component.

3. The method according to claim 1, wherein said initial amount of solvent added to dissolve said recovered polymerized form of said component is sufficient to maintain said recovered polymerized form of said component dissolved in said initial amount of solvent in solution.

4. The method according to claim 1, wherein said solvent is an acetate solution.

5. The method according to claim 4, wherein said acetate solution has a pH of about 4.

6. The method according to claim 1, wherein said initial amount of solvent added to dissolve said recovered polymerized form of said component is about 80 vol. % of said predetermined total amount of solvent, and said amount of additional solvent added to said s recovered polymerized form of said component is about 20 vol. % of said predetermined total amount of solvent.

7. The method according to claim 1, wherein said step of adding said additional solvent to said recovered polymerized form of said component comprises the steps of adding a first predetermined portion of said additional solvent to said recovered polymerized form of said component, and subsequently adding a second predetermined portion of said additional solvent to said recovered polymerized form of said component.

8. The method according to claim 1, wherein said conditions for catalyzing said polymerized form of said component from said blood or plasma comprises contacting said blood or plasma with an enzyme for catalyzing formation of said polymerized form of said component.

9. The method according to claim 1, wherein said blood or plasma component is fibrinogen.

10. The method according to claim 9, wherein said conditions for catalyzing said polymerized form of said fibrinogen comprises contacting said fibrinogen with an enzyme for catalyzing cleavage of fibrinopeptides A and/or B from said fibrinogen.

11. The method according to claim 10, wherein said enzyme is batroxobin.

12. The method according to claim 1, wherein said step of recovering said polymerized form of said component comprises the steps of depositing onto a wall of a chamber of a centrifuge apparatus said polymerized form of said component.

13. The method according to claim 12, wherein said step of depositing said polymerized form of said component onto said wall of said chamber comprises the step of spinning said chamber in said centrifuge apparatus while said polymerized form of said component is present therein.

* * * * *